(12) United States Patent
Zhong et al.

(10) Patent No.: US 6,770,039 B2
(45) Date of Patent: Aug. 3, 2004

(54) METHOD TO REDUCE TISSUE INJURY IN SHOCK WAVE LITHOTRIPSY

(75) Inventors: Pei Zhong, Chapel Hill, NC (US);
Yufeng Zhou, Durham, NC (US);
Franklin H. Cocks, Durham, NC (US);
Glenn M. Preminger, Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 10/290,718

(22) Filed: Nov. 8, 2002

(65) Prior Publication Data

US 2003/0093013 A1 May 15, 2003

Related U.S. Application Data

(60) Provisional application No. 60/338,070, filed on Nov. 9, 2001.

(51) Int. Cl.[7] ............................................. A61B 17/225
(52) U.S. Cl. .......................................................... 601/4
(58) Field of Search .......................... 601/2–4; 600/439; 367/141, 142, 147, 151, 157, 168, 175; 606/128

(56) References Cited

U.S. PATENT DOCUMENTS

| | | |
|---|---|---|
| 3,942,531 A | 3/1976 | Hoff et al. |
| 4,655,220 A | 4/1987 | Hahn et al. |
| 4,664,111 A | 5/1987 | Reichenberger |
| 4,821,730 A | 4/1989 | Wurster et al. |
| 4,888,746 A | 12/1989 | Wurster et al. |
| 5,209,221 A | 5/1993 | Riedlinger |
| 5,219,401 A | 6/1993 | Cathignol et al. |
| 5,582,578 A | 12/1996 | Zhong et al. |
| 5,800,365 A | 9/1998 | Zhong et al. |
| 6,298,264 B1 | 10/2001 | Zhong et al. |

Primary Examiner—Ruth S. Smith
(74) Attorney, Agent, or Firm—Jenkins, Wilson & Taylor, P.A.

(57) ABSTRACT

A method to reduce vascular injury produced by lithotripter shock waves comprising the use of particular multi-pulsed shock waves which comminute human concretions with reduced vascular damage.

12 Claims, 3 Drawing Sheets

METHOD TO REDUCE TISSUE INJURY IN SHOCK WAVE LITHOTRIPSY

RELATED APPLICATIONS

This application claims the benefit of U.S. Provisional Patent Application Serial No. 60/338,070, filed Nov. 9, 2001; the disclosure of which is incorporated herein by reference in its entirety.

GOVERNMENT INTEREST

This invention was made with Government support under Grant No. DK52985 awarded by the National Institutes of Health. The Government has certain rights in the invention.

TECHNICAL FIELD

The present invention relates to a method for comminuting concretions located within a living body using time-synchronized, multi-pulsed acoustic shock waves, to suppress cavitation bubble expansion for the reduction of vascular injury produced by lithotripter shock waves.

BACKGROUND OF THE INVENTION

Extracorporeally generated shock waves are presently used clinically for the fragmentation and comminution of kidney and ureteral stones, a process called shock wave lithotripsy (SWL). Despite its widespread success, SWL as it is currently carried out can also cause renal injury, such as hematuria, kidney enlargement, and renal and perirenal hemorrhage and hematomas. Furthermore, the long-term clinical consequence of SWL on renal function is still under investigation. Renal injury in SWL is primarily vascular lesions, characterized by extensive damage of the endothelial cells and the rupture of blood vessels, with capillary and small blood vessels much more susceptible to SWL injury than large vessels. While most patients with normal renal function recover well following lithotripsy, there are subgroups of patients who are at much higher risk for chronic SWL injury. These include patients with solitary kidneys, pre-existing hypertension, and, in particular, pediatric and elderly patients.

In the past two decades, shock wave lithotripsy (SWL) has been used routinely as a treatment modality for the majority of stone patients. Clinical and animal studies, however, have also demonstrated that SWL is accompanied by some forms of renal injury, such as hematuria, formation of diffuse hemorrhage and multiple hematomas within the renal parenchyma, perirenal fat, and subcapsular connective tissue, as well as kidney edema. The injury is primarily vascular lesions, with extensive damage to the endothelial cells and rupture of capillaries and small blood vessels. In young adult patients, the vascular injury associated with SWL only affects about 2.0% of their functional renal mass. Therefore, most of these patients recover following the treatment without significant clinical consequences. There are, however, subgroups of patients who are at much higher risk for chronic injury following SWL. Therefore, there is clearly a clinical need to improve the safety of SWL treatment.

One primary mechanism that leads to vascular injury in SWL is the mechanical dilation of the capillaries and small blood vessels by the large, rapid intraluminal expansion of cavitation bubbles. It is now known that if such a large intraluminal bubble expansion is suppressed and, for example by the inversion of the lithotripter shock waveform, vascular injury will be minimized. Normal lithotripter shock waves consist of a leading compressive wave followed by a tensile wave. In an inverted lithotripter shock wave, the tensile wave precedes the compressive wave. Unfortunately, inverted lithotripter shock waves do not break up kidney stones; and therefore cannot be successfully used for SWL. Clearly, there is a need for SWL that can significantly suppress cavitation bubble expansion while maintaining effective stone comminution efficiency.

Zhong et al. in U.S. Pat. No. 5,582,578 disclose a method for the comminution of concretions in vivo by controlling and concentrating cavitation energy, utilizing two shock wave pulses. In the method disclosed by Zhong et al. the second pulse forces the complete collapse of cavitation bubble cluster produced by the first pulse in such a way that the cavitation collapse energy is directed towards the target concretion and thereby reducing tissue injury caused by random collapse of cavitation bubbles. However, in the method disclosed by Zhong et al., the second shock wave pulse is produced after a delay of more than 50 μs delay from the time of the first shock wave arrives at the focus of a lithotripter and therefore causes complete bubble collapse because at this point in time cavitation bubbles are at or near to their maximum expansion. However, Zhong et al. do not disclose or discuss the beneficial effect of an interpulse delay that is shorter than 50 μs that has now been unexpectedly and surprisingly discovered to restrain the further expansion of cavitation bubbles.

SUMMARY OF THE INVENTION

The present invention provides a method for generating time-synchronized, multi-pulsed shock waves, which are controlled in their respective pressure amplitudes and which have a specified extremely short interpulse time delay (0.5 to 21 microseconds) and specified pressure relationships between the compressive and tensile components of the individual pulses to provide a means of inducing an inertial cavitation bubble cluster while suppressing the growth, but not the collapse, of cavitation bubbles in tissue surrounding the target concretion in vivo to achieve stone comminution with reduced tissue injury.

It is therefore an object of the present invention to control precisely the profile and sequence of the acoustic shock wave pulses produced by a lithotripter to achieve effective stone comminution in SWL while at the same time drastically reducing tissue injury.

Some of the objects of the invention having been stated hereinabove, and which are addressed in whole or in part by the present invention, other objects will become evident as the description proceeds when taken in connection with the accompanying drawings as best described hereinbelow.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description, taken in connection with the drawings described in detail below.

REFERRED EMBODIMENTS OF THE INVENTION

Physics of the Method

Figure 1:
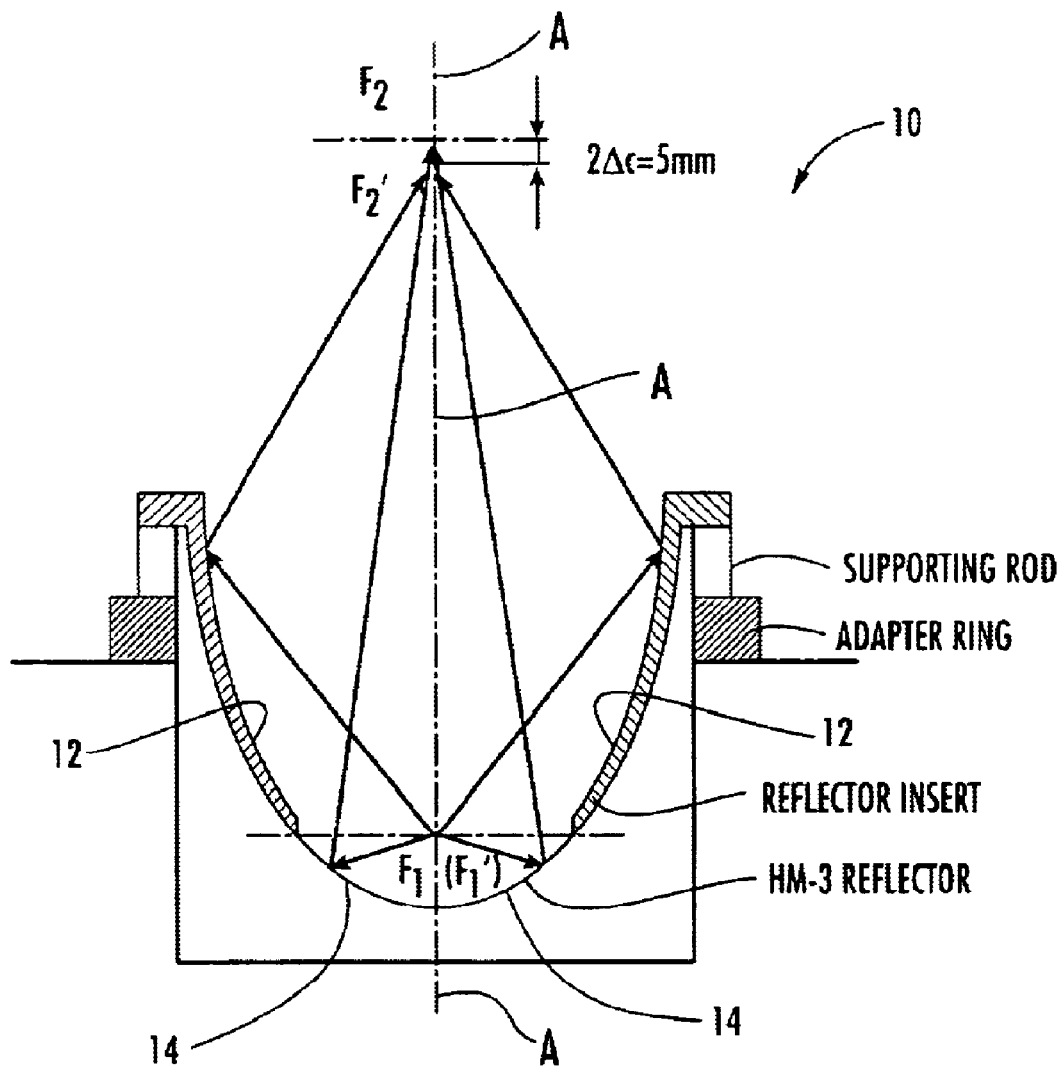
FIG. 1 is a schematic drawing of the reflector of a DORNIER HM-3 lithotripter modified to achieve the aims of the method of the current invention. As shown, the DORNIER HM-3 lithotripter, which is one of the most widely used clinical lithotripters in the world, consists essentially of a spark gap electrode and a truncated ellipse of revolution to focus the shock wave produced by the electrode.

The expansion of cavitation bubbles in SWL is determined primarily by the tensile component of a lithotripter shock wave. To suppress cavitation without compromising stone comminution capability of a lithotripter, it has been discovered that a secondary compression wave can be used to cancel partially the tensile component of a lithotripter shock wave and suppresses the radial expansion of the bubble. Applicants have found, using high-speed photography, that the initial expansion of a bubble induced in a small blood vessel phantom during SWL could be quickly stopped by the constraint of the vessel wall once bubble-vessel contact was established. Presumably, the kinetic energy associated with the expanding bubble at the moment of the contact would be largely converted into the mechanical energy associated with the circumferential dilation of the vessel wall, which eventually led to rupture. If the bubble were produced in a free field without constraint, the kinetic energy would be converted into the potential energy of the bubble at its maximum expansion. Therefore, on a first order approximation, the energy absorbed by the vessel wall can be estimated by the difference in potential energy, $E_P$, between the bubble at the size of the vessel lumen and the bubble at its maximum expansion in a free field:

$$Ep = \int_{R_v}^{R_{max}} P_0 4\pi R^2 dR = \frac{4}{3}\pi(R_{max}^3 - R_v^3)P_0, \quad (1)$$

where R is bubble radius, $R_{max}$ is the bubble radius at maximum expansion, $R_v$ is the radius of the vessel lumen, and $P_0$ is the ambient pressure of the surrounding liquid. For small blood vessels ($R_v$<0.1 mm, and thus $R_v/R_{max}$<0.01), $E_p$ is proportional to $R_{max}^3$ in a typical lithotripter field. Therefore, a small reduction in $R_{max}$ (for example, 30%) could lead to a significant decrease in $E_p$ (~66%) and, consequently, the propensity for vessel rupture. This is the physical basis for utilizing an in situ pulse superposition technique to reduce the potential of vascular injury in SWL, which has now been discovered.

The present invention is based on two important features in lithotripter shock wave propagation and bubble dynamics. It has now been discovered that the maximum peak positive pressure of a lithotripter is not produced exactly at the geometric focus, but rather about 5.0–10.0 millimeters further away from the focus. This is caused by the nonlinear propagation of lithotripter shock wave in tissue. It has now been discovered that if the lithotripter focusing means is modified to focus the shock wave a few millimeters before the geometric focus, a higher pressure can be achieved at the stone surface thus increasing the stone fragmentation efficiency. This effect has not been taken into consideration in the design of clinical lithotripters. A second important consideration is the reduction of bubble expansion by in situ pulse superposition.

To reduce the adverse effects of SWL, it is important to understand as fully as maybe possible the mechanisms whereby vascular injuries are produced. Most previous research suggests that cavitation, the formation and subsequent expansion and collapse of gas/vapor bubbles in the acoustic field of a lithotripter, may play an important role in the vascular injury in SWL. In particular, shock wave-bubble interaction with resultant microjet formation has been implicated as a mechanism by which the perforation of a vessel wall, primarily in medium-to-large size blood vessels, could be produced. However, asymmetric collapse of a bubble with resultant high-speed microjet formation may not be produced if the bubble size is small (for example, less than 0.5 millimeters in diameter) due to the reduced cross-sectional area for shock wave-bubble interaction. Thus, for the majority of vascular injury in SWL, which is often observed in capillaries and small blood vessels, a different mechanism must be responsible. Based on results from animal studies and theoretical calculations of SWL-induced bubble dynamics in blood, applicants have discovered that the expansion of intraluminal bubbles in small blood vessels is significantly constrained, and their subsequent collapse severely weakened. Conversely, the large, rapid expansion of an intraluminal bubble significantly dilates a vessel wall, which leads to rupture if the resultant circumferential stress exceeds the tensile failure strength of the vessel. This hypothesis was confirmed using vessel phantoms made of cellulose hollow fibers.

Bubble dynamics in SWL has been found to be strongly influenced by the pressure waveform and pulse sequence. Hence, applicants found it possible to optimize the waveform and sequence of lithotripter shock waves to produce more desirable cavitation activity for better stone comminution and reduced tissue injury by creating time-synchronized multi-pulsed shock waves, each with proper time duration and interpulse spacing. Applicants have developed a method of modifying the pressure waveform of the lithotripter shock wave to suppress the large intraluminal bubble expansion in SWL without compromising stone comminution. This invention is based on the discovery that a weak or compressive wave superimposing on or immediately following the tensile component of a lithotripter shock wave can suppress the expansion of cavitation bubbles induced in a lithotripter field. Although applicants have conducted all tests described herein on a DORNIER HM-3 lithotripter, it should be understood that the time-synchronized, multi-pulsed shock wave method of the invention is not limited thereto, but is applicable to all lithotripters that utilize acoustic shock waves for the comminution of stones, without regard to the means which are used to produce the initial shock wave.

The Method of the Invention

The key features of the current invention involve the specific sequence of time-synchronized, multi-pulse shock waves, independent of how the shock waves are produced. For example, the shock waves can be produced by electrohydraulic, electromagnetic, or piezoelectric means. Similarly, various acoustic focusing means can be used to separate a single shock wave into time-synchronized, multi-pulse shock waves at the focus of the lithotripter apparatus. For example, acoustic lenses or time-sequenced activation of multiple piezoelectric elements as well as modifications to ellipsoidal reflectors in electrohydraulic lithotripters may be used to produce the needed time-synchronized, multi-pulse shock waves. In the following, the modification of the ellipsoidal reflector of a DORNIER HM-3 lithotripter to achieve time-synchronized, multi-pulsed shock waves is disclosed as one embodiment of the present invention. It is understood that the invention disclosed herewith is independent of the physical means used to produce the time-synchronized, multi-pulsed shock wave pulses, which can be produced using an acoustic source that has either electrohydraulic, electromagnetic, or piezoelectric means, or combinations thereof, for generating shock waves. Further, the invention can comprise, for example, a staged, multi-surface ellipsoidal reflector; a staged, multi-surface parabolic reflector; or a staged, multi-surface acoustic lens.

Referring to FIGS. 1 and 2, one preferred embodiment of the invention is illustrated by the particular case of a DORNIER HM-3 electrohydraulic shook wave lithatripter 10 that is provided with an insert 12, which covers a large portion, more than 50% but less than 90% of the interior surface of the original DORNIER HM-3 reflector 14, to generate a leading lithotripter shook wave toward $F_2'$, the secondary focus, located on the lithotripter axis A by a distance of less than 24 millimeters below $F_2$, the primary focus, following each spark discharge at the first focus of the ellipsoidal reflector 14 $F_1$, which is also the same physical position as the first focus, $F_1'$, for the inserted reflector 12). From the same spark discharge, reflection from the remaining portion of the DORNIER HM-3 reflector will generate a weaker second acoustic shock wave pulse at an interpulse time delay between 0.5 and 21 microseconds from the leading itthotripter shock wave, which is the first acoustic shock wave pulse. In the case of an acoustic source that uses an electrohydraulic shock wave generating system, this interpulse delay can be controlled by appropri ate selection of the geometry of the Insert 12, which is inserted to cover a large portion of the interior surface of the DORNIER HM-3 reflector 14. In one preferred embodiment, the distance between the geometric foci of the DORNIER HM-3 and insert reflectors is $F_2-F_2'2c-2c'=2\Delta c$. It can be shown that interpulse delay $\Delta t$ is determined by $2a-(2a'2\Delta c)=C_0\Delta t$ where a, b, c are the semi-major axis, semi-minor axis, and half focal length of the original DORNIER HM-3 ellipsoidal reflector ($c^2=a^2-b^2$), and a', b', c' are the corresponding values for the inserted reflector, respectively, and $C_0$ is the sound speed in water.

In a preferred embodiment of the present invention, applicants determined the interpulse delay and the minimal thickness of the insert reflector 12 at a horizontal plane across $F_1$ as a function of $\Delta a$ (=a-a') and $\Delta c$ (=c-c'). Applicants found that insert reflectors 12 with a minimal thickness at the lower rim of the reflector insert $\Delta x$ in the range of 3.0–8.0 mm can be used to produce an interpulse delay $\Delta t$ in the range of 2.0–7.0 $\mu s$. It has been unexpectedly discovered that these interpulse time delays are very effective in reducing the tensile pressure of the lithotripter shock wave and concomitantly suppressing cavitation bubble expansion. It has been found that the preferred interpulse delay is preferably between 0.5 and 21.0 $\mu s$ and the first and second acoustic shock wave pulses together should preferably have a total time duration of not more than 55 microseconds, as measured from the beginning the first pulse to the end of the second pulse.

This invention of the preferred timing and intensity of the time-synchronized, multi-pulsed shock waves for kidney stone comminution with reduced tissue injury has been confirmed by a preferred embodiment in which a fabricated insert 12 that can be fitted to cover more than 80% of the interior surface area of an original DORNIER HM-3 reflector. In other preferred embodiments between 50% and 90% of the interior surface area of the original DORNiER HM-3 reflector can be covered by the insert 12. The basic idea is to divide the original DORNIER HM-3 reflector surface into two parts, with one large reflecting surface 12 generating a leading lithotripter shock wave and the remaining small reflecting surface producing a weak compressive wave, sufficient to suppress the large bubble expansion induced by the tensile pressure of the lithotripter shook wave.

Figures 2A, 2B:
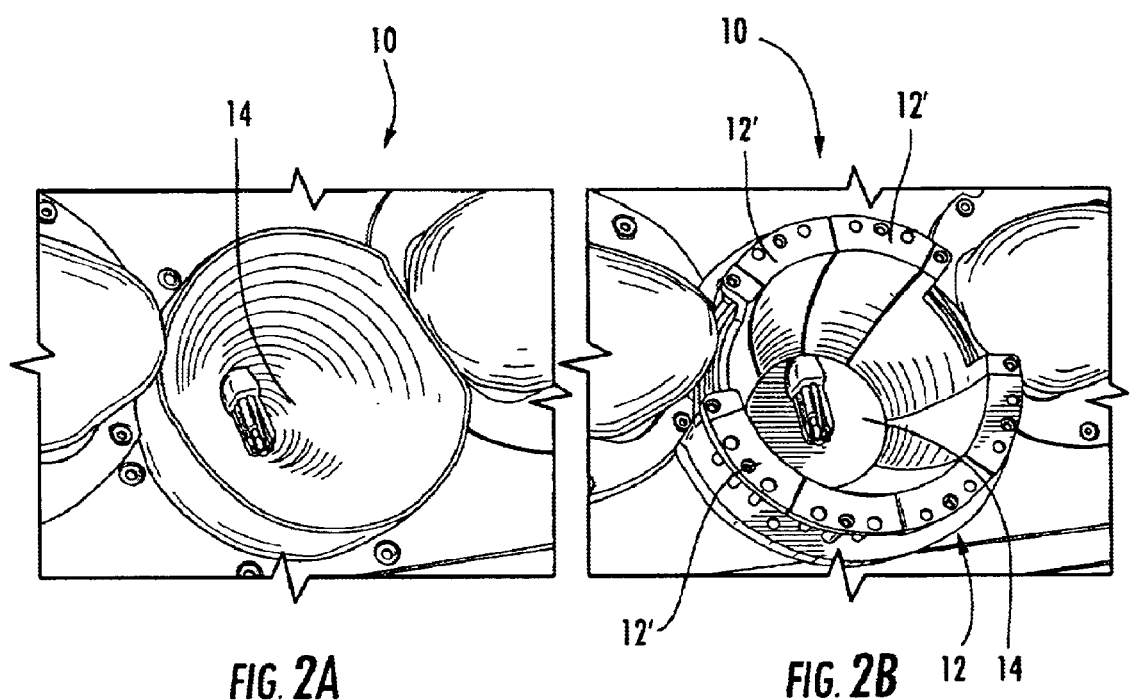
FIGS. 2A, 2B are photographs showing the original DORNIER HM-3 reflector and the upgraded reflector, respectively, wherein the reflector insert of the upgraded reflector is fabricated in eight segments with each segment individually attachable to the original reflector by means of an adapter ring and position pins, screws and supporting rods.

In the prototype as shown in FIGS. 2A, 2B, the inserted reflector 12 was divided into individual segments 12' so that various combinations of the first and second reflecting surfaces can be created. Also, the secondary focus $F_2'$ of the inserted reflector 12 is 5.0 mm below the primary focus ($F_2$) of the DORNIER HM-3 reflector 14 and the differences in major axes is 11.4 mm, yielding an interpulse delay of about 4 $\mu s$ based on linear acoustic wave propagation. In other preferred embodiments, the interpulse delay can be varied from 0.5 to 21 microseconds.

Figure 3:
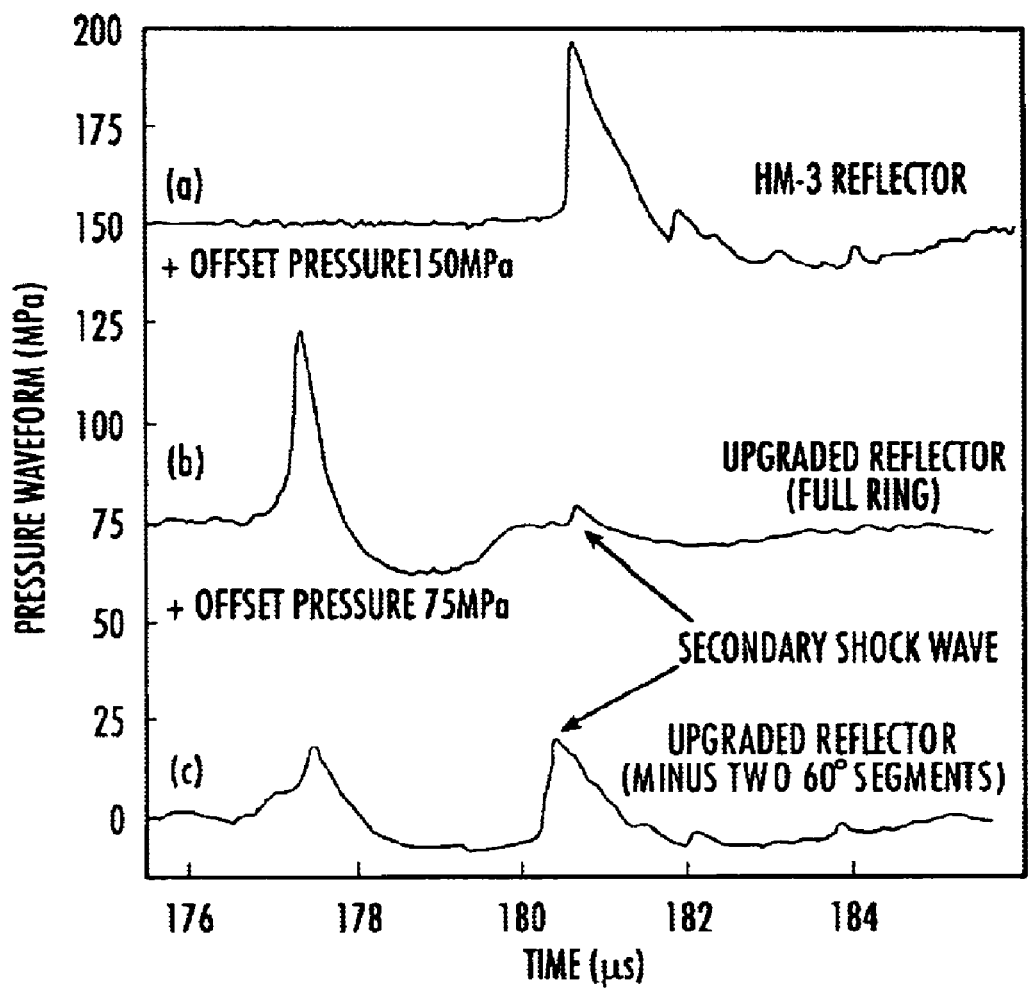
FIG. 3 is a graph showing representative pressure wave forms of the lithotripter shock waves generated by using (a) the original DORNIER HM-3 reflector; (b) the altered reflector (full array); and (c) the altered reflector (without two 60° segments) all at an output voltage of 24 kV.

FIG. 3 shows the pressure waveform measured at $F_2$ using a membrane hydrophone. It can be seen that with the modified reflector, a second pulse appears in about 4.0 $\mu s$ following the leading lithotripter shock wave. This second pulse truncates a portion of the tensile component of the lithotripter shock wave, resulted in a weak compressive peak, which suppresses the large expansion of cavitation bubbles induced by the tensile wave of the lithotripter shock wave.

Using a passive cavitation detection method, the collapse time ($t_c$) of the bubble clusters produced by the original and the modified DORNIER HM-3 was measured along the shock wave axis (Z-axis) both at $F_2$ and at $-5.0$ mm and $-10.0$ mm before $F_2$. These results showed that the modified reflector leads to a dramatic reduction in $t_c$. In particular, while the value of $t_c$ increases prefocally using the original HM-3 reflector, it remains unchanged using the modified reflector. At z=−10.0 mm, the reduction in $t_c$ is about 42% from the original to the modified reflector. It has now been discovered that this significantly suppressed bubble expansion greatly reduces the potential for vascular injury in the subcapsular connective tissue and renal parenchyma along the shock wave blast path.

The impact of applicants' modified reflector for the lithotripter on vascular injury and stone comminution was further evaluated using hollow fiber vessel phantom and plaster-of-Paris stone models. At 24 kV, while using the original reflector, rupture of the vessel phantom was produced after only 30 shocks, while no rupture of the vessel phantom was observed after 200 shocks using the altered reflector, modified and upgraded to produce time-synchronized, multi-pulsed shock waves. Stone comminution, on the other hand, was still comparable to that produced by the original reflector.

This particular embodiment is specifically related to the DORNIER HM3 lithotripter 10. However, it will be appreciated that applicants' discovery of the critical role that is played by the specific time sequences used for multi-pulsed shock waves to reduce tissue injury in SWL is independent of the means by which these multi-pulsed shock waves are generated. Therefore, those skilled in the art can modify other shock wave lithotripter systems, whether they be electrohydraulic, electromagnetic, or piezoelectric in nature so that these lithotripter systems too can produce the specific time sequences which applicants have now discovered and disclosed. Applicants have used inserts 12 that are inserted into an ellipsoidal reflector 14 of a DORNIER HM3 electrohydraulic lithotripter 10 to produce the specific multi-pulsed shock waves needed to reduce tissue injury while still comminuting kidney stones or other human concretions. However, those skilled in the art of electromagnetic lithotripters can modify the acoustic lenses used with such electromagnetic lithotripters to produce the specific multi-pulsed shock waves that have been discovered and disclosed herein by applicants. Similarly, those skilled in the art of piezoelectric lithotripters can modify the time sequence of firing the individual piezoelectric elements used in such piezoelectric lithotripters to produce the same specific multi-pulsed shock waves that have been discovered and disclosed herein by applicants.

In the preferred embodiment of the present invention for comminuting with reduced tissue injury a concretion located within a living body, the steps of creating multi-pulsed shock waves comprise essentially the following; (a) creating a multi-pulsed shock wave that consists of a leading, first, acoustic shock wave nulse and a weaker second acoustic shock wave pulsed, (b) focusing the leading acoustic shock wave pulse to a secondary focus $F_2'$, and focusing the second acoustic shook wave pulse to the primary focus. $F_2$ where a concretion within a living body is located, to increase at this primary focus the compressive pressure amplitude of this leading acoustic shock wave pulse to at least 10 megapascals and its tensile pressure amplitude to at least 0.5 megapascals, in order to produce an inertial cavitation bubble cluster embracing the concretion: and (c) focusing the second acoustic shock wave pulse to the primary focus, whereby the second acoustic shock wave pulse is increased in its compressive pressure amplitude to at least 5 megapascals and its tensile pressure amplitude to no more than 8 megapascals, wherein the primary focus and secondary focus are separated by a distance of 0 to 24 millimeters so that the first and second acoustic shock wave pulses are separated in arrival time at the primary focus by an interpulse delay of no less than 0.5 microseconds, nor more than 21 microseconds. It has now been found that the second acoustic shock wave pulse serves to suppress substantially the expansion of cavitation bubbles induced by the first acoustic shock wave pulse in tissues surrounding the primary focus, whereby the concretion Is comminuted with reduced tissue injury.

It will be understood that various details of the invention may be changed without departing from the scope of the invention. Furthermore, the foregoing description is for the purpose of illustration only, and not for the purpose of limitation, as the invention is defined by the claims as set forth hereinafter.

What is claimed is:

1. A method for comminuting with reduced tissue injury a concretion located within a living body, said method consisting essentially of the steps of:
   (a) creating a multi-pulsed shock wave by an acoustic source, said acoustic source having an axis, said multi-pulsed shock wave consisting of a leading acoustic shock wave pulse and a weaker second acoustic shock wave pulse;
   (b) focusing said leading acoustic shock wave pulse to a secondary focus and focusing said second acoustic shock wave pulse to a primary focus where said concretion is located, said primary focus and said secondary focus are aligned on said axis of said acoustic source, said secondary focus being closer than said primary focus to said acoustic source by a distance of less than 24 millimeters, said first and second acoustic shock wave pulses thereby being separated in arrival time at said primary focus by an interpulse delay between 0.5 and 21 microseconds, said leading acoustic shock wave pulse upon its arrival at said primary focus having a compressive pressure amplitude of at least 10 megapascals and having a tensile pressure amplitude of at least 0.5 megapascals to produce an inertial cavitation bubble cluster, said inertial bubble cluster embracing said concretion; and
   (c) said second acoustic shock wave pulse upon its arrival said primary focus having a compressive pressure amplitude of at least 5 megapascals and having a tensile pressure amplitude of less than 8 megapascals, and said second acoustic shock wave pulse thereby serving to substantially suppress expansion of said inertial cavitation bubble duster induced by said leading acoustic shock wave pulse in tissues surrounding said concretion, whereby said concretion is comminuted with a concomitant reduction in tissue injury.

2. The method of claim 1, comprising providing an electrohydraulic shock wave generating system as the acoustic source.

3. The method of claim 1, comprising providing an electromagnetic shock wave generating system as the acoustic source.

4. The method of claim 1, comprising providing a piezoelectric shock wave generating system as the acoustic source.

5. The method of claim 1, comprising providing a compound shock wave generating system consisting of a combination of electrohydraulic and piezoelectric shock wave generating systems as the acoustic source.

6. The method of claim 1, comprising providing a compound shock wave generating system consisting of a combination of electromagnetic and piezoelectric shock wave generating systems as the acoustic source.

7. The method of claim 1, comprising providing a compound shock wave generating system consisting of a combination of electrohydraulic and electromagnetic shock wave generating systems as the acoustic source.

8. The method of claim 1, comprising providing a staged, multi-surfaced ellipsoidal reflector to produce the interpulse delay.

9. The method of claim 1, comprising providing a staged, multi-surfaced parabolic reflector to produce the interpulse delay.

10. The method of claim 1, comprising providing a staged, multi-surfaced acoustic lens to produce the interpulse delay.

11. The method of claim 1, wherein said multi-pulsed shock wave is produced by the steps of:
   (a) providing an electrohydraulic shook wave lithotripter having a reflector, said reflector having an insert fitted within said reflector, said reflector having an interior surface and said insert covering a substantial portion of said interior surface of said reflector, and providing a reflector portion not covered by said insert;
   (b) generating a leading lithotripter shock wave from said insert following each spark discharge of said electrohydraulic shock wave lithotripter, and
   (c) generating a second weaker compressive shock wave from said reflector portion not covered by said insert with each spark discharge of said eleotrohydraulic shock wave lithotripter, whereby said second weaker compressive shock wave serves to substantially suppress expansion of cavitation bubbles and resulting vascular injury normally induced by said eleotrohydraulic shock wave lithotripter.

12. The method of claim 11, comprising providing an insert covering more than 50% of said interior surface of said reflector.

* * * * *